United States Patent [19]
Milne et al.

[11] Patent Number: 5,840,667
[45] Date of Patent: Nov. 24, 1998

[54] BLEACH ACTIVATORS

[75] Inventors: Neal James Milne, Chester; Jonathan Mercer Watkins, Deeside, both of Great Britain

[73] Assignee: Warwick International Group, Ltd., Holywell, Great Britain

[21] Appl. No.: 776,965

[22] PCT Filed: Aug. 3, 1995

[86] PCT No.: PCT/GB95/01847

§ 371 Date: Feb. 5, 1997

§ 102(e) Date: Feb. 5, 1997

[87] PCT Pub. No.: WO96/04244

PCT Pub. Date: Feb. 15, 1996

[30] Foreign Application Priority Data

Aug. 5, 1994 [GB] United Kingdom .................... 9415871
Jan. 6, 1995 [GB] United Kingdom .................... 9500223

[51] Int. Cl.$^6$ ...................... C07C 400/40; C07C 271/22; C11D 3/39
[52] U.S. Cl. ................................ 510/376; 562/2
[58] Field of Search ........................ 252/186.26, 186.38, 252/186.39, 186.4, 186.41, 186.42, 186.43; 562/2; 510/367, 376

[56] References Cited

U.S. PATENT DOCUMENTS

| | | | |
|---|---|---|---|
| 2,855,436 | 10/1958 | Rekker | 260/562 |
| 3,078,301 | 2/1963 | Taub | 260/482 |
| 4,617,417 | 10/1986 | Conley et al. | 560/29 |
| 4,634,551 | 1/1987 | Burns et al. | 252/102 |

FOREIGN PATENT DOCUMENTS

| | | |
|---|---|---|
| 0144290 | 6/1985 | European Pat. Off. . |
| 0170386 | 2/1986 | European Pat. Off. . |
| 0325289 | 7/1989 | European Pat. Off. . |
| 0332050 | 9/1989 | European Pat. Off. . |
| 0426217 | 5/1991 | European Pat. Off. . |
| 0458327 | 11/1991 | European Pat. Off. . |
| 0485928 | 5/1992 | European Pat. Off. . |
| 0564250 | 10/1993 | European Pat. Off. . |
| 959204 | 5/1964 | United Kingdom . |
| 1465451 | 2/1977 | United Kingdom . |
| 1472154 | 5/1977 | United Kingdom . |
| 2231871 | 11/1990 | United Kingdom . |
| 94/28104 | 12/1994 | WIPO . |

*Primary Examiner*—Mukund J. Shah
*Assistant Examiner*—Deepak R. Rao
*Attorney, Agent, or Firm*—Ostrolenk, Faber, Gerb & Soffen, LLP

[57] ABSTRACT

A bleach composition comprises a peroxygen bleach source (for instance hydrogen peroxide, a perborate or a percarbonate salt) and an activator of the formula I:

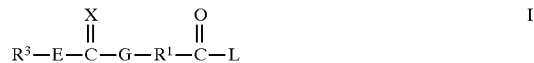

in which X is O or S;
one of E and G is —A— and the other is —N($R^2$)—;
A is —O— or —S—;
$R^1$ is a $C_{1-50}$ alkylene group (including cyclo alkylene), optionally interrupted by an arylene group and/or by one or more ether, ester, anhydride, thioether, secondary or tertiary amine, amide or imide linkage, an arylene group or an alkarylene group;
$R^2$, is selected from H, alkyl, aralkyl, alkaryl and aryl;
$R^3$ is alkyl, aralkyl, alkaryl or aryl, or, when E is —N($R^2$)—, H;
in which $R^2$ and $R^3$ can be joined so as to form a heterocyclic ring with the atoms to which they are attached, and/or in which $R^1$ can be joined with $R^2$ or $R^3$; and
L is a leaving group which may optionally be joined to any of $R^1$, $R^2$ and $R^3$. The activator gives the composition good bleaching at low temperatures, minimal dye and fabric damage and which bleach a wide range of oxidisable stains.

26 Claims, No Drawings

BLEACH ACTIVATORS

This application is a 371 of PCT 16895/01847 filed Aug. 3, 1995.

The present invention relates to activators for use in conjunction with peroxygen bleaches to improve low temperature bleaching, in particular laundry detergent compositions, textile bleaches, hard surface cleaners, pulp bleaching and other bleaching environments. The activator compounds contain carbamate groups.

In EP-A-0,170,386, peroxy acid bleaching compounds include in the peracid molecule an amide group. The peracids may be generated in situ by the reaction between an activator, that is a compound in which the perhydroxyl group of the percarboxylic acid is replaced by a leaving group, and a peroxygen source, such as an inorganic persalt. The activator and persalt may be incorporated into the same detergent composition together with other components. Alternatively, stable magnesium salts of the percarboxylic acid may be incorporated into a detergent.

In EP-A-0,458,327, ureido peroxy carboxylic acids are described. In EP-A-0485928, the ureido percarboxylic acids are synthesised from carbamoyl lactams by cleavage of the N—C bonds of the lactam ring. The cleavage reaction is carried out in concentrated sulphuric acid or methane sulphonic acid, followed by addition of concentrated aqueous hydrogen peroxide.

Other nitrogen containing bleach activator compounds include phthalimide derivatives, for instance N-alkyl derivatives in which the alkyl group includes a percarboxylic group. Such compounds are described in EP-A-0,325,289 and EP-A-0,325,288, as well as EP-A-0,166,041. Other nitrogen containing derivatives include isatoic anhydride derivatives such as disclosed in EP-A-0,332,050. Other cyclic nitrogen containing activators are the 2-substituted benzoxazine-4-ones such as described in EP-A-0,332,294.

Compounds falling within the scope of formula I herein are known compounds. For instance in U.S. Pat. No. 4617417, compounds of the formula I in which $R^2$ is H and A is O and in which the group at the position represented by L is alkoxy are described as intermediates for making diones which are known as cardiotonic agents. In EP-A-0561758, similar compounds are described as intermediates which are saponified and subsequently have the alkoxy carbonyl protecting group removed to form chiral β-amino acids. In GB-A-0959204, similar compounds are intermediates in the synthesis of herbicides which are carbamic esters in which the group represented by L in formula I is an alkyl amino group. In GB-A-1472154, similar compounds are hydrogenated and subsequently have a benzyloxycarbonyl protecting group for the amine functionality removed, in the synthesis of pyroglutamyl compounds which have antidepressive activity. In U.S. Pat. No. 2855436, similar compounds in which $R^1$ is 1,2-phenylene are cyclised to form a condensed ring system including an isatoic anhydride structure, which are subsequently used as synthetic intermediates for making insecticides. In EP-A-0144290, Ω-amino carboxylic acids are first of all treated to protect the amine group using benzyloxycarbonyl group and subsequently esterified and used as an intermediate in the formulation of a polypeptide having anti-hypertensive properties.

Compounds of the formula I as herein defined in which the group represented by L is an alkoxy group, and which X is either O or S and A is O or S themselves have herbicidal properties. Such properties are also described in GB-A-1465451. In GB-A-2231871, such compounds are said to be useful in the thickening or solidification of oily liquids, for example in cosmetics, pharmacy and paint industry. In U.S. Pat. No. 3078301, such compounds are used as plasticisers for polyvinyl resins.

There is still a need for improved bleach activator compounds which give good bleaching at low temperatures, but which have minimal dye damage and fabric damage properties and bleach a wide range of stains.

A new composition according to the present invention, which is of particular use as a bleach composition, comprises a peroxygen bleach precursor and a compound of the formula I:

in which X is O or S;
one of E and G is —A— and the other is —N($R^2$)—;
A is —O— or —S—;
$R^1$ is a $C_{1-50}$ alkylene group (including cyclo alkylene), optionally interrupted by an arylene group and/or by one or more ether, ester, anhydride, thioether, secondary or tertiary amine, amide or imide linkage, an arylene group or an alkarylene group;
$R^2$, is selected from H, alkyl, aralkyl, alkaryl and aryl;
$R^3$ is alkyl, alkaryl, aralkyl or aryl, or, when E is —N($R^2$)—, H;
in which $R^2$ and $R^3$ can be joined so as to form a heterocyclic ring with the atoms to which they are attached, and/or in which $R^1$ can be joined with $R^2$ or $R^3$; and
L is a leaving group which may optionally be joined to any of $R^1$, $R^2$ and $R^3$.

In the general formula I when E is —N($R^2$)—, $R^3$ is selected from H, alkyl, aralkyl, alkaryl and aryl.

In the general formula I, X is preferably O.

In a preferred aspect, the molecular weight of the compound of formula I is less than 1000.

In one preferred aspect of the present invention, A is —O—. Preferably E is —A—; so that G is —N($R^2$)—.

$R^1$ preferably includes 1–12 carbon atoms. Preferred examples are unsubstituted $C_{1-6}$ alkylene and 1,2-arylene groups, preferably unsubstituted arylene.

Alkyl groups in any of $R^2$ and $R^3$ are preferably lower alkyl, for instance $C_{1-8}$-g-alkyl, more preferably $C_{1-6}$-alkyl. Preferred examples are $C_{1-2}$-alkyl. $R^2$ may be hydrogen.

In one preferred aspect of the invention $R^3$ and $R^2$ are joined to make a 5 or 6 membered ring with the moiety

For instance, $R^2$ and $R^3$ together are unsubstituted $C_2$-alkylene.

Any alkyl groups (including alkylene) may include unsaturated bonds, for instance ethylenically unsaturated bonds. Thus, where the context permits, alkyl includes alkenyl and alkynyl groups. It is preferred that alkyl groups do not include unsaturated carbon—carbon bonds. Any alkyl or aryl groups in any of the groups $R^1$, $R^2$ and $R^3$ may be substituted, for instance with groups to improve the water solubility of the compound, provided these do not detract from the performance of the activator. Substituents can include hydroxyl, =N—$R^5$, in which $R^5$ is selected from any of the groups represented by $R^2$ and is preferably lower alkyl, as well as amine, acyl, acyloxy, alkoxy, aryl, aroyl, aryloxy, aroyloxy, halogen, amido, and imido groups.

Alkyl and alkylene groups may be branched or straight substituted nitrogen atoms or carbonyl groups.

The leaving group L is preferably a compound the conjugate acid of which has a $pK_a$ in the range 4–13, preferably 7–11, most preferably 8–11. Preferred leaving groups are:

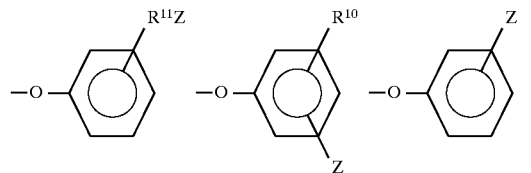

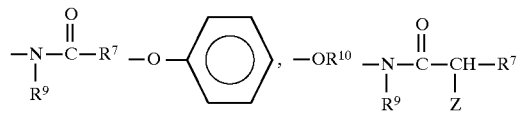

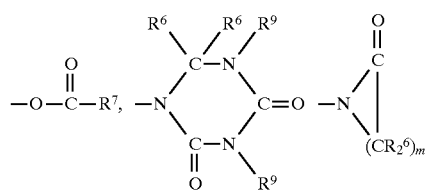

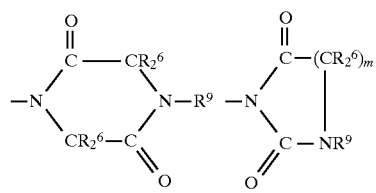

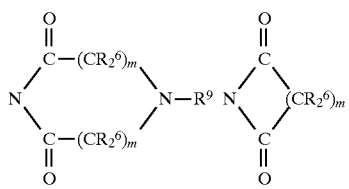

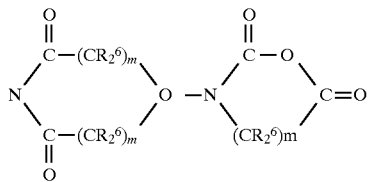

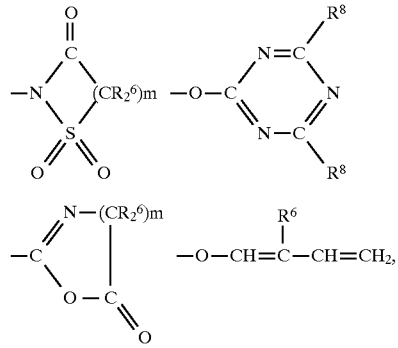

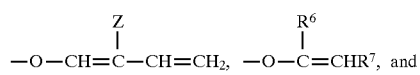

-continued

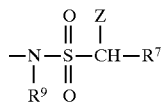

$R^6$, $R^7$, $R^8$ and $R^9$ are each selected from H, alkyl (preferably lower alkyl, most preferably methyl) and/or and aryl and may be joined to other groups in the moiety L or in any of $R^1$ to $R^4$ to form a cyclic activating compound;
$R^{10}$ is an alkyl chain containing from 1 to 8 carbon atoms;
$R^{11}$ is lower alkylene, preferably $C_1$ to $C_4$-alkylene
Z is H or a solubilising group.
The preferred solubilising groups Z are $-SO_3^-M^+$, $-COO^-M^+$, $-SO_4^-M^+$, $(-N^+R^4{}_3)X^-$

and (and most preferably $-SO_3^-M^+$ and $-COO^-M^+$) wherein $R^4$ is an alkyl chain containing from 1 to 4 carbon atoms, M is a cation, with sodium and potassium being most preferred, and X is a halide, hydroxide, methylsulfate or acetate anion.

L is preferably $OR^{10}$, OPh or

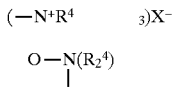

where $R^7$ is lower alkyl or is lower alkylene such that together with $R^1$, $R^7$ forms a trivalent lower alkyl group (i.e. is joined to a lower alkylene group $R^1$) and $R^{10}$ is lower, preferably $C_{1-6}$-alkyl.

The present invention provides further a process in which a compound of the formula I is contacted in aqueous solution with a peroxygen bleach precursor to form the compound of the formula II

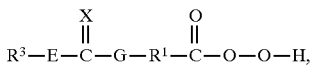

in which $R^1$, E, G. X and $R^3$ have the meanings mentioned above in connection with the activator compound or $R^2$ or $R^3$ is $R^4R^{13}H$ and $R^{13}$ corresponds to the group L defined above wherein L is joined to $R^2$ or $R^3$ as the case may be and $R^4$ is alkylene
or arylene, or $R^1$ is

where $R^{12}$ is trifunctional alkyl or aryl and $R^{13}$ corresponds to the group L defined above when L is joined to $R^1$ (i.e. as derived from an activator compound of the formula I in which L is joined to one of $R^1$, $R^2$ and $R^3$), or its anionic form (i.e. in a salt).

The peroxygen bleach precursor may be hydrogen peroxide or may be an inorganic persalt, for instance a percarbonate, perborate, persulfate, alternatively it may be an organic peroxygen compound such as benzoyl peroxide, or other percarboxylic acid compound.

The process is generally carried out in conditions generally applicable to bleaching conditions, for instance used in laundry detergent liquors or cleaners used in a domestic environment. The process is generally carried out at an alkaline pH, for instance in the range 9–13, but may also be carried out at an acidic pH or a pH in the range from acidic to $pK_a$ of the percarboxylic acid of the formula II.

Some compounds of the formula II are novel compounds. The present invention also covers those compounds. In a preferred class, $R^1$ is an alkylene group. Preferably E is A.

Instead of generating a percarboxylic acid in situ in the bleaching liquor, the new percarboxylic acids or salts thereof, may be dissolved directly into an aqueous solution to form the bleaching liquor. Magnesium salts of the percarboxylic acid of the novel compounds of formula II are particularly useful as they are relatively storage stable. The present invention covers compositions containing those salts.

Where an activator of the formula I is included in a storage stable composition, as in the preferred composition, the composition preferably also contains a peroxygen bleach precursor, such as are described above.

The compositions may further contain components conventionally used in bleaching compositions, for instance pH-adjusters, builders, surfactants/wetting agents which may be cationic, anionic, amphoteric or nonionic, as well as disinfectants, biocides, slimicides, enzymes, inhibitors or radical scavengers, abrasives, colouring agents, soil suspending agents, optical brightening agents, fabric softeners, etc. The activator of the formula I may be used in conjunction with co-activators such as tetraacetyl ethylene diamine (TAED), tetraacetyl glycol uril (TAGU) or alkanoyloxybenzene sulphonates, or with preformed peracids, such as PAP (N-phthalimido perhexanoic acid), or with transition metal catalysts or organic catalysts such as enzymes or any other activating moiety. The peracid of the invention may be used as the magnesium salt. The peracid, when formed in situ from activator and peroxygen source, may react with further activator to form a diacyl peroxide which is an oxidising species.

The compositions may be in any suitable form, such as powder, granular, tablet, cake, or liquid, which may be aqueous or non-aqueous based. When the compositions are in the preferred granular form, the activator and peroxygen source are preferably contained in separate granule components. These may, in turn, be produced by known granulation techniques, for instance techniques such as are described in EP-A-0,238,341, EP-A-0,299,599, EP-A-0,482,806, and preferably comprise binders, for instance meltable binders such as nonionic surfactants, or starch or cellulose-based binders such as carboxy methyl cellulose, or synthetic polymer binders such as acrylate ester binders. The granules may be produced. by the usual techniques of agglomeration, granulation, extrusion of a dispersion in a molten binder or of a moistened powder blend, optionally followed by spheronisation and/or coating for additional storage stability.

The bleach activator composition and preferably the granules containing bleach activator preferably contains a bleach stabiliser, that is a sequestrant, such as a poly(methylene phosphonic acid) sequestrant or a polycarboxylic acid sequestrant. Suitable sequestrants are in particular alkylene polyamine poly(methylene phosphonic acids) and their salts.

The activator granules may contain other agents to improve dissolution or dispersion, for instance effervescent compounds, swelling agents, water soluble salts etc.

The invention is illustrated in the following examples:

EXAMPLE 1

Preparation of N-Benzyloxycarbonyl Aspartic Anhydride (Compound A)

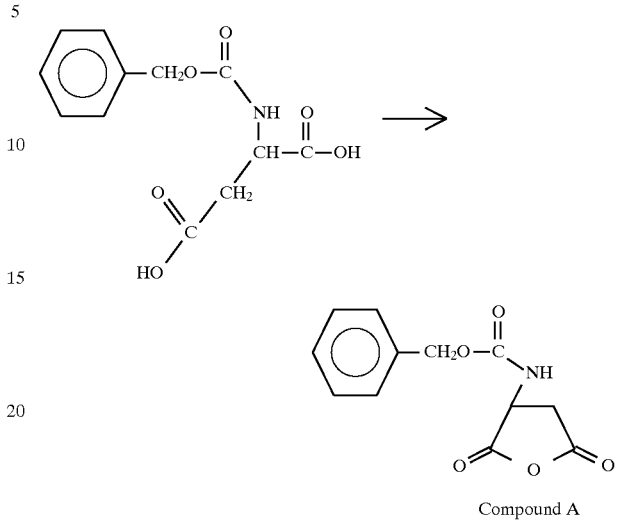

Compound A

The above illustrated starting compound which is commercially available N-CBZ aspartic acid (205.7 g, 0.77 mol) was added to acetic anhydride (300 ml). This mixture was stirred at 75° C. for 4 hours. The excess acetic anhydride and acetic acid byproduct were distilled from the mixture under reduced pressure and the residue was recrystallised from hot dichloromethane. The product was collected by filtration, washed with hexane and dried at ambient temperature under reduced pressure to give a white fluffy solid.

Yield=137.7 g (72%)

Infra-red spectrum and nmr spectrum were consistent with the required structure, compound A, in which $R^1$ is methylene and is joined to a group L which is a group

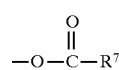

in which $R^7$ is methylene, E is —O—, G is —N($R^2$)— in which $R^2$ is H, $R^3$ is benzyl and X is O.

EXAMPLE 2

Preparation of Phenyl N-Ethoxycarbonyl Sarcosinate (Compound B)

i) Preparation of ethyl N-ethoxycarbonyl sarcosinate

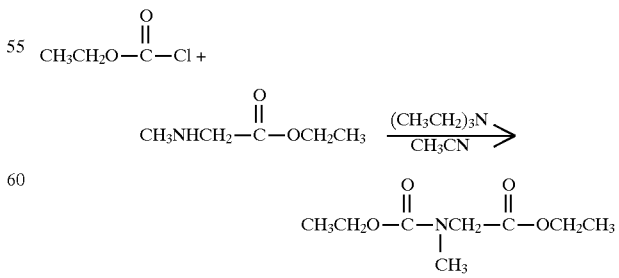

A stirring mixture of ethyl sarcosinate hydrochloride (200 g, 1.30 mol) (which is commercially available), triethylamine (303.4 g 3.00 mol) and acetonitrile (900 ml) was cooled using an ice/water bath. Ethyl chloroformate (170 g, 1.57 mol) was dissolved in acetonitrile (200 ml) and added in portions to the reaction mixture. Once the addition was complete, the resulting mixture was held at reflux for four hours. Once the reaction mixture had cooled to ambient temperature, it was filtered and then the bulk of the acetonitrile was removed by distillation under reduced pressure. The residue was taken up in ether (600 ml) and washed with aqueous hydrochlorid acid (5%, 1×400 ml), water (1–400 ml) aqueous sodium hydroxide solution (5%, 1–400 ml) and water (1–400 ml). The ethereal solution was dried over anhydrous sodium sulphate and then filtered. The ether was removed by distillation under reduced pressure to give the product as an orange liquid.

Yield=191 g (78%)

ii) Preparation of N-ethoxycarbonyl sarcosine

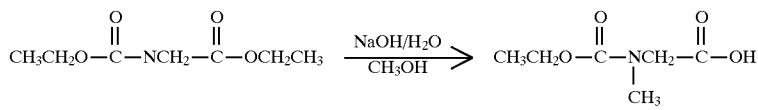

to:

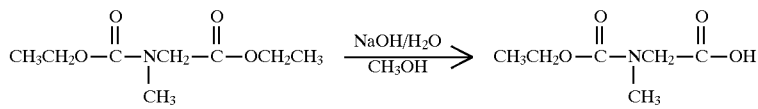

Ethyl N-ethoxycarbonyl sarcosinate (191 g, 1.01 mol) was dissolved in methanol (400 ml) and sodium hydroxide (45.4 g, 1.14 mol) was dissolved in deionized water. The two solutions were mixed together and stirred for four hours. The reaction liquor was concentrated by distillation of a methanol/ethanol mixture under reduced pressure. Deionized water (250 ml) was added to the residue. This aqueous solution was washed with ether (2×200 ml) and then acidified with hydrochloric acid to pH 1. The product was extracted with ether (3–200 ml) and the extracts were combined and dried over anhydrous magnesium sulphate. The ethereal solution was filtered and the ether was removed by distillation under reduced pressure to give the crude product as a yellow liquid. This liquid was distilled at 5 mbar to give the product as a clear colourless oil, bp 135°–140° C.

Yield=138 g (84%)

Infra-red spectrum and nmr spectrum were consistent with the required structure.

iii) Preparation of phenyl N-ethoxycarbonyl sarcosinate

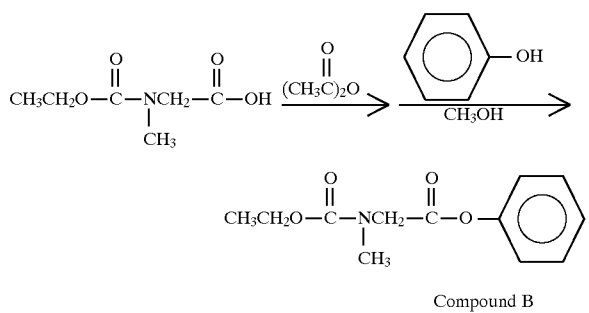

Compound B

N-ethoxycarbonyl sarcosine (60.0 g, 0.372 mol) and acetic anhydride (200 ml) were heated together at 80° C. for two hours. The excess acetic anhydride and acetic acid byproduct were removed by distillation under reduced pressure to give the intermediate anhydride. Phenol (20.0 g, 0.213 mol) was added and the mixture was heated at 80° C. for nine hours. The reaction mixture was dissolved in ether (150 ml) and washed with aqueous sodium hydroxide solution (5%, 2×200 ml), water (1×100 ml) and aqueous sodium chloride soution (10%, 1×100 ml). The ethereal solution was dried over anhydrous sodium sulphate and then filtered. The ether was removed by distillation under reduced pressure to give the crude product as a pale yellow syrup. This syrup was distilled at 1 mbar to give the product as a clear colourless oil, bp 104° C.

Yield=28.7 g (65%)

HPLC purity=98 area %

Infra-red spectrum and nmr spectrum were consistent with the required structure, compound B, in which L is OPh, $R^1$ is methylene, G is —N($R^2$)— in which $R^2$ is methyl, E is —O—, X is O and $R^1$ is ethyl.

EXAMPLES 3 and 4

Wash tests

The bleach activators prepared in examples 1 and 2 were tested for washing performance, comparisons being made using: (i) a blank incorporating no bleach activator and (ii) a comparative known bleach activator.

Swatches of 100% cotton 12 cm×12 cm were stained using the stains listed below:

| | |
|---|---|
| WIL Tea | Tea prepared by Warwick International Group Limited |
| Red wine | Red wine stains |
| BC1 | Tea stains with clay |
| BC2 | Coffee stains |
| BC3 | Tea stains |
| BC4 | Curry stains |
| BC5 | Red beet stains |
| AS4 | Chlorophyll in vegetable oil stains |

These stains are useful to give an indication of the bleaching power of formulations incorporating bleach activator. AS4 is particularly good at indicating bleaching performance on oily stains.

Wash tests were carried out under conditions typical of European laundry washing conditions. Wash tests were carried out at 40° C. using cold fill Wascator FOM 71 MP machines, programmed to BS 4923 (HLCC) wash programmes.

Formulations incorporating the activator for testing were prepared containing 22.4 g PBS4 (sodium perborate tetrahydrate), 124.5 g IEC standard base detergent and a weight of activator calculated to give the same moles peracid release as 2% by weight TAED assuming 1 mole of activator releases 1 mole of peracid and taking into account the purity of the activator compound synthesised as determined by HPLC. Formulations were dosed at 7.5 g/l wash water via the dispensing drawer of the machines.

During the wash tests the swatches were tagged to 2.5 kg polyester backing cloth, using plastic tags. After washing the swatches were removed and ironed dry prior to reading reflectance measurements to assess stain removal. Stain removal was assessed as a percentage brightness and calculated using the equation.

$$\text{Stain removal} = \frac{(RA - RB)}{(RS - RB)} \times 100$$

where RA is the reflectance of the washed swatch, RB is the reflectance of the unwashed swatch and RS is the reflectance of an unstained swatch. Reflectance was measured with U.V. at 420 nm using a Spectroflash 500 Spectrophotometer machine.

Due to variations in swatch make up, all evaluations were run compared to a TAED tetracetylethylenediamine standard, as well as a blank incorporating no activator.

TABLE

EUROPEAN WASHES AT 40°
STAIN REMOVAL (% z - BRIGHTNESS:SPECTRAFLASH

| | FORMULATION | | | |
|---|---|---|---|---|
| SWATCH | Blank | Ex3 | Ex4 | TAED Std |
| Red Wine | 36.0 | 37.6 | 39.5 | 42.2 |
| WIL Tea | 21.2 | 29.2 | 30.5 | 31.8 |
| BC1 | 5.4 | 5.1 | 8.0 | 7.6 |
| BC2 | 7.4 | 5.8 | 12.0 | 9.4 |
| BC3 | 8.8 | 9.0 | 14.2 | 14.0 |
| BC4 | 8.9 | 6.9 | 11.1 | 8.5 |
| BC5 | 7.6 | 7.3 | 10.0 | 10.2 |
| AS4 | 11.5 | 9.6 | 10.4 | 11.8 |

FORMULATIONS:
1. Blank: 22.4 g PBS4, 124.5 g IEC Base.
2. TAED Std: 3.0 Uncoated TAED, 22.4 g PBS4, 124.5 g IEC Base.
3. EX3: 6.560 g Compound A, 22.4 g PBS4, 124.5 g IEC Base.
4. Ex4: 6.372 g Compound B, 22.4 g PBS4, 124.5 g IEC Base.

Wash test results are given in the Table, from which it can be seen that activators according to the invention boost the perborate bleaching and in some cases outperform TAED which is itself a very good bleach activator.

We claim:

1. A composition comprising a peroxygen bleach precursor and a compound of formula I:

$$R^3—E—C(X)—G—R^1—C(O)—L \qquad (I)$$

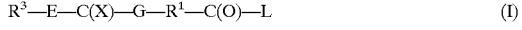

in which

X is O or S;

one of E and G is —A— and the other is —N($R^2$)—;

A is —O— or —S—;

$R^1$ is selected from the group consisting of arylene, aliphatic hydrocarbon-arylene and $C_{1-50}$ divalent aliphatic or cycloaliphatic hydrocarbon which is optionally interrupted by at least one group selected from the group consisting of arylene, ether, ester, anhydride, thioether, secondary or tertiary amine, amide and imide linkage;

$R^2$ is selected from the group consisting of H, aliphatic hydrocarbon, aliphatic hydrocarbon-aryl, aryl-aliphatic hydrocarbon and aryl;

$R^3$ is selected from the group consisting of aliphatic hydrocarbon, aliphatic hydrocarbon-, aryl-aliphatic hydrocarbon or aryl, or, when E is —N($R^2$)—, H; and L is a leaving group the conjugate acid of which has a p$K_a$ of 4 to 13, optionally connected to at least one of $R^1$, $R^2$ and $R^3$.

2. A composition according to claim 1 in which X is O.

3. A composition according to claim 2 in which A is —O—.

4. A composition according to claim 1 in which A is —O—.

5. A composition according to claim 1 in which $R^2$ and $R^3$ are alkyl.

6. A composition according to claim 5 in which $R^2$ and $R^3$ are $C_{1-8}$-alkyl.

7. A composition according to claim 6 in which $R^2$ and $R^3$ are $C_{1-2}$-alkyl.

8. A composition according to claim 1 in which L is $OR^{10}$, OPh or O—C(O)—$R^7$ wherein $R^7$ is $C_{1-8}$ alkyl or is $C_{1-6}$ alkylene and is joined to $R^1$ and wherein $R^{10}$ is lower alkyl.

9. A composition according to claim 8 in which $R^{10}$ is $C_{1-6}$alkyl.

10. A composition according to claim 1 in which the compound of the formula I has a molecular weight of less than 1000.

11. A composition according to claim 1 in which the peroxygen bleach precursor is hydrogen peroxide or an inorganic persalt.

12. A composition according to claim 11 in which the peroxygen bleach precursor is sodium perborate or sodium percarbonate.

13. A composition according to claim 1 which is a concentrate which is dilutable with water to provide a bleaching liquor.

14. A composition according to claim 8 in which $R^7$ is joined to $R^1$.

15. A method in which a compound of formula I:

$$R^3—E—C(X)—G—R^1—C(O)—L \qquad (I)$$

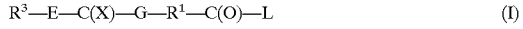

in which

X is O or S;

one of E and G is —A— and the other is —N($R^2$)—;

A is —O— or —S—;

$R^1$ is selected from the group consisting of arylene, aliphatic hydrocarbon-arylene and $C_{1-50}$ divalent aliphatic or cycloaliphatic hydrocarbon, which is optionally interrupted by at least one group selected from the group consisting of arylene, ether, ester, anhydride, thioether, secondary or tertiary amine, amide and imide linkage;

$R^2$ is selected from the group consisting of H, aliphatic hydrocarbon, aliphatic hydrocarbon-aryl, aryl-aliphatic hydrocarbon and aryl;

$R^3$ is selected from the group consisting of aliphatic hydrocarbon, aliphatic hydrocarbon-aryl, aryl-aliphatic hydrocarbon or aryl, or, when E is —N($R^2$)—, H; and L is a leaving group the conjugate acid of which has a p$K_a$, of 4 to 13, optionally connected to at least one of $R^1$, $R^2$ and $R^3$ is contacted in aqueous solution with a peroxygen bleach source.

16. A method according to claim 15 in which X and A are O.

17. A method according to claim 15 in which $R^2$ and $R^3$ are $C_{1-8}$-alkyl.

18. A method according to claim 15 in which L is $OR^{10}$, OPh or O—C(O)—$R^7$ wherein $R^7$ is $C_{1-8}$ alkyl or is $C_{1-6}$ alkylene and is joined to $R^1$ and wherein $R^{10}$ is lower alkyl.

19. A method according to claim 15 in which the compound of the formula I has a molecular weight of less than 1000.

20. A percarboxylic acid of the formula II or a salt thereof $$R^3\text{—}E\text{—}C(X)\text{—}G\text{—}R^1\text{—}C(O)\text{—}OOH \qquad (II)$$

in which

X is O or S;

one of E and G is —A— and the other is —$N(R^2)$—;

A is —O— or —S—;

$R^1$ is selected from the group consisting of arylene, aliphatic hydrocarbon-arylene and $C_{1-50}$ divalent aliphatic or cycloaliphatic hydrocarbon, which is optionally interrupted by at least one group selected from the group consisting of arylene, ether, ester, anhydride, thioether, secondary and tertiary amine, amide and imide linkages;

$R^2$ is selected from the group consisting of H, aliphatic hydrocarbon, aryl-aliphatic hydrocarbon, aliphatic hydrocarbon-aryl and aryl;

$R^3$ is selected from the group consisting of aliphatic hydrocarbon, aryl-aliphatic hydrocarbon, aliphatic hydrocarbon-aryl and aryl, or, when E is —$N(R^2)$—, is H.

21. A percarboxylic acid compound according to claim 20 in which $R^1$ is an alkylene group.

22. A percarboxylic acid compound according to claim 20 in which A is —O—.

23. A compound according to claim 20 in which X is O.

24. A compound according to claim 20 in which $R^2$ and $R^3$ are alkyl.

25. A compound according to claim 20 in which $R^2$ and $R^3$ are $C_{1-8}$-alkyl.

26. A compound according to claim 20 in which $R^2$ and $R^3$ are $C_{1-2}$-alkyl.

* * * * *